United States Patent
Meyer et al.

(10) Patent No.: US 11,179,075 B2
(45) Date of Patent: Nov. 23, 2021

(54) REGIONAL OXIMETRY SENSOR INTERFACE

(71) Applicant: Nonin Medical, Inc., Plymouth, MN (US)

(72) Inventors: David A. Meyer, Rockford, MN (US); Timothy L. Johnson, Plymouth, MN (US); Bryant Austin Jones, Minneapolis, MN (US)

(73) Assignee: Nonin Medical, Inc., Plymouth, MN (US)

(*) Notice: Subject to any disclaimer, the term of this patent is extended or adjusted under 35 U.S.C. 154(b) by 0 days.

(21) Appl. No.: 14/082,975

(22) Filed: Nov. 18, 2013

(65) Prior Publication Data

US 2015/0141780 A1 May 21, 2015

(51) Int. Cl.
*A61B 5/1455* (2006.01)
*A61B 5/0205* (2006.01)
(Continued)

(52) U.S. Cl.
CPC ...... *A61B 5/14552* (2013.01); *A61B 5/02055* (2013.01); *A61B 5/002* (2013.01); *A61B 5/14535* (2013.01); *A61B 2560/045* (2013.01)

(58) Field of Classification Search
CPC .............. A61B 5/1495; A61B 5/14551; A61B 5/14552; A61B 5/6826; A61B 5/6838;
(Continued)

(56) References Cited

U.S. PATENT DOCUMENTS

| | | |
|---|---|---|
| 5,810,724 A | 9/1998 | Gronvall |
| 6,622,034 B1 | 9/2003 | Gorski et al. |

(Continued)

FOREIGN PATENT DOCUMENTS

WO  WO-2014159723 A2  10/2014

OTHER PUBLICATIONS

U.S. Appl. No. 13/829,158, Final Office Action dated Jan. 4, 2016, 12 pgs.

(Continued)

*Primary Examiner* — Chu Chuan Liu
(74) *Attorney, Agent, or Firm* — Schwegman Lundberg & Woessner, P.A.

(57) ABSTRACT

A system includes a sensor, a second connector, a local processor, a first telemetry module, a second telemetry module, and a remote processor. The sensor is coupled to a cord and the cord has a first connector. The second connector is coupled to a housing. The second connector is configured to mate with the first connector. The local processor is coupled to the second connector and disposed in the housing. The local processor is configured to execute instructions stored in a local memory. The local memory is disposed in the housing. The local processor is configured to generate calculated data based on a signal received at the second connector. The signal corresponds to a parameter measured by the sensor. The first telemetry module is coupled to the local processor and is configured to wirelessly communicate the calculated data. The second telemetry module is configured to communicate with the first telemetry module. The remote processor is coupled to the second telemetry module. The remote processor is configured to generate output data based on the calculated data.

18 Claims, 2 Drawing Sheets

(51) Int. Cl.
*A61B 5/00* (2006.01)
*A61B 5/145* (2006.01)

(58) Field of Classification Search
CPC ... A61B 5/0002; A61B 5/0205; A61B 5/1455; A61B 5/14553
See application file for complete search history.

(56) References Cited

U.S. PATENT DOCUMENTS

| | | | |
|---|---|---|---|
| 7,671,351 B2 | 3/2010 | Setlak et al. | |
| 7,844,315 B2* | 11/2010 | Al-Ali | A61B 5/02438 600/323 |
| 8,301,232 B2 | 10/2012 | Albert et al. | |
| 9,693,697 B2 | 7/2017 | Tal et al. | |
| 9,895,090 B2 | 2/2018 | Johnson et al. | |
| 10,188,329 B2 | 1/2019 | Isaacson et al. | |
| 10,709,368 B2 | 7/2020 | Johnson et al. | |
| 2002/0082489 A1 | 6/2002 | Casciani et al. | |
| 2002/0116797 A1 | 8/2002 | Modgil et al. | |
| 2003/0181798 A1* | 9/2003 | Al-Ali | A61B 5/7475 600/324 |
| 2006/0238358 A1* | 10/2006 | Al-Ali | A61B 5/14552 340/573.1 |
| 2008/0139908 A1 | 6/2008 | Kurth | |
| 2009/0105605 A1* | 4/2009 | Abreu | 600/549 |
| 2009/0163787 A1 | 6/2009 | Mannheimer et al. | |
| 2010/0010326 A1 | 1/2010 | Dalvi et al. | |
| 2010/0125188 A1* | 5/2010 | Schilling et al. | 600/336 |
| 2010/0240972 A1 | 9/2010 | Neal | |
| 2010/0312080 A1 | 12/2010 | Isaacson | |
| 2010/0331631 A1* | 12/2010 | MacLaughlin | 600/301 |
| 2011/0077473 A1* | 3/2011 | Lisogurski | 600/301 |
| 2011/0112387 A1* | 5/2011 | Li | A61B 5/14551 600/324 |
| 2011/0224518 A1 | 9/2011 | Tindi et al. | |
| 2012/0059267 A1 | 3/2012 | Lamego et al. | |
| 2014/0200054 A1 | 7/2014 | Fraden | |
| 2014/0275885 A1 | 9/2014 | Isaacson et al. | |
| 2015/0099951 A1* | 4/2015 | Al-Ali | A61B 5/14552 600/323 |
| 2015/0141779 A1 | 5/2015 | Johnson et al. | |
| 2018/0140238 A1 | 5/2018 | Johnson et al. | |

OTHER PUBLICATIONS

U.S. Appl. No. 13/829,158, Non Final Office Action dated Jul. 6, 2015, 11 pgs.
U.S. Appl. No. 13/829,158, Response filed Dec. 7, 2015 to Non Final Office Action dated Jul. 6, 2015, 12 pgs.
U.S. Appl. No. 14/082,950, Non Final Office Action dated Dec. 16, 2015, 14 pgs.
Application Serial No. PCT/US2014/024906, International Preliminary Report on Patentability dated Sep. 24, 2015, 7 pgs.
International Application Serial No. PCT/US2014/024906, International Search Report dated Sep. 16, 2014, 2 pgs.
International Application Serial No. PCT/US2014/024906, Written Opinion dated Sep. 16, 2014, 5 pgs.
U.S. Appl. No. 13/829,158, Final Office Action dated Jul. 28, 2016, 13 pgs.
U.S. Appl. No. 13/829,158, Response filed Jul. 5, 2016 to Final Office Action dated Jan. 4, 2016, 10 pgs.
U.S. Appl. No. 14/082,950, Final Office Action dated Aug. 16, 2016, 11 pgs.
U.S. Appl. No. 14/082,950, Response filed Jun. 16, 2016 to Non Final Office Action dated Dec. 16, 2015, 11 pgs.
European Application Serial No. 14775821.3, Response filed May 2, 2016 to Communication pursuant to Rules 161(2) and 162 EPC dated Oct. 22, 2015, 14 pgs.
"U.S. Appl. No. 13/829,158, Response filed Jan. 30, 2017 to Final Office Action dated Jul. 18, 2016", 16 pgs.
"U.S. Appl. No. 13/829,158, Examiner Interview Summary dated Dec. 19, 2016", 4 pgs.
"U.S. Appl. No. 13/829,158, Non Final Office Action dated Feb. 22, 2017", 12 pgs.
"U.S. Appl. No. 14/082,950, Response filed Feb. 16, 2017 to Advisory Action dated Feb. 8, 2017", 16 pgs.
"U.S. Appl. No. 14/082,950, Advisory Action dated Feb. 8, 2017", 3 pgs.
"U.S. Appl. No. 14/082,950, Non Final Office Action dated Mar. 7, 2017", 13 pgs.
"U.S. Appl. No. 14/082,950, Response filed Jan. 17, 2017 to Final Office Action dated Aug. 16, 2016", 13 pgs.
"Eropean Application Serial No. 14775821.3, Extended European Search Report dated Oct. 18, 2016", 8 pgs.
U.S. Appl. No. 13/829,158, Non Final Office Action dated Dec. 15, 2017, 6 pgs.
U.S. Appl. No. 13/829,158, Response filed Aug. 22, 2017 to Non Final Office Action dated Feb. 22, 2017, 18 pgs.
U.S. Appl. No. 14/082,950 Examiner Interview Summary dated Jun. 22, 2017, 3 pgs.
U.S. Appl. No. 14/082,950, Notice of Allowance dated Oct. 5, 2017, 7 pgs.
U.S. Appl. No. 14/082,950, Response filed Aug. 7, 2017 to Non Final Office Action dated Mar. 7, 2017, 15 pgs.
"U.S. Appl. No. 13/829,158, Notice of Allowance dated Sep. 19, 2018", 9 pgs.
"U.S. Appl. No. 13/829,158, Response fled Apr. 16, 2018 to Non Final Office Action dated Dec. 15, 2017", 12 pgs.
U.S. Appl. No. 16/235,884, filed Dec. 28, 2018, Self-Contained Regional Oximetry.
U.S. Appl. No. 15/872,779, filed Jan. 16, 2018, Regional Oximetry Sleeve for Mobile Device.
"U.S. Appl. No. 15/872,779, Non Final Office Action dated Jun. 27, 2019", 6 pgs.
U.S. Appl. No. 15/872,779, Notice of Allowance dated Mar. 10, 2020, 5 pgs.
U.S. Appl. No. 15/872,779, Response filed Dec. 27, 2019 to Non Final Office Action dated Jun. 27, 2019, 5 pgs.
U.S. Appl. No. 16/903,283, filed Jun. 16, 2020, Regional Oximetry Sleeve for Mobile Device.

* cited by examiner

REGIONAL OXIMETRY SENSOR INTERFACE

BACKGROUND

A measure of regional oximetry can provide an indication as to tissue health. Existing technology for measuring regional oximetry is inadequate. One example includes an optical sensor coupled by a wire to a separate processing module. The sensor may be secured to the patient by an adhesive or by a strap encircling the patient and is tethered by wire to the processing module.

This arrangement of a sensor and a processor module with a connecting wire is unsatisfactory for certain applications. For example, in an emergency situation or a battlefield environment, the separate nature of the modules and the connecting wire can be inconvenient and may be prone to failure.

OVERVIEW

The present inventors have recognized, among other things, that a problem to be solved can include providing a system for measuring regional oximetry based on a rapidly established temporary coupling to the tissue and using a mobile computing device. The present subject matter can help provide a solution to this problem, such as by a system including a sensor module that can be coupled to a mobile device and manually positioned at a tissue site. The mobile device can display results and can communicate the data to a remote device using wireless communication.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
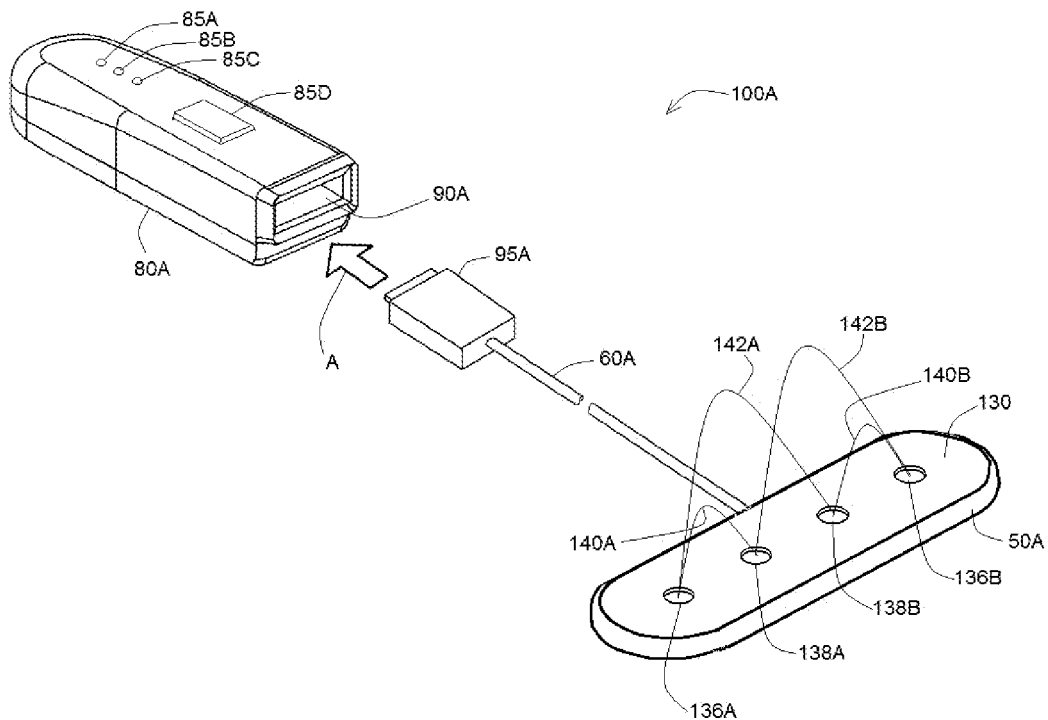
FIG. 1 illustrates a view of a portable device and a sensor, according to one example.

FIG. 1 illustrates system 100A including portable device 80A and sensor 50A, according to one example. Portable device 80A includes a housing having connector 90A. Connector 90A is coupled to the housing and is configured to mate with complementary connector 95A, as shown by arrow A.

Portable device 80A includes elements 85A, 85B, 85C, and 85D on a surface of the housing. Elements 85A, 85B, 85C, and 85D can include user-operable controls or switches or can include visible indicators (such as a light emitting diode, LED, or a visible display). Elements 85A, 85B, 85C, and 85D can indicate a device condition (such as readiness for a measurement, battery charge state, or availability of wireless communication channel), or can indicate measured data corresponding to a signal from sensor 50A.

Connector 95A is coupled by link 60A to sensor 50A. Link 60A, in one example, includes a length of flexible, multiconductor electric wire.

Sensor 50A, in the example shown, includes at least one transducer configured to provide an electric signal corresponding to a measured parameter. The measured parameter can include regional oximetry, temperature, acceleration, pressure or other parameter. Examples of other parameters or conditions that can be measured using a suitable transducer and programming, include: regional saturation (rSO2); hemoglobin (Hb) concentration in tissue; tissue temperature; $SpO_2$; total hemoglobin (tHb); hematocrit; anemia; $CO_2$; COHb; MetHb; pH; respiration; perfusion; apnea; pulse wave velocity; blood pressure; interstitial pressure; arterial stiffness; intracranial pressure; intrauterine pressure/contractions; glucose; cardiac output; bilirubin; hydration; hematoma; vascular compliance; tissue viability; malaria; blood cancer; thrombocytopenia (low platelet count); sepsis; thrombosis; or compartment syndrome.

In addition, a suitable algorithm executing on a processor and a suitable sensor module can provide data as to a material property of an object or as to a surface. This can include processing based on data corresponding to an optical measurement, a mechanical measurement, an acoustic measurement, or an electrical measurement. For example, data can correspond to an event counter, an event marker (time mark), a density measurement, a conductivity measurement, a concentration measurement, a color measurement, or a light level measurement.

In one example, sensor 50A includes contact surface 130. Contact surface 130 has a sensor module including emitter 138A and emitter 138B. Emitter 138A emits light into tissue that is received by detector 136A along short pathway 140A and light that is received by detector 136B along long pathway 142B. Emitter 138B emits light that is received by detector 136B along short pathway 140B and light that is received by detector 136A along long pathway 142A. Light received by detector 136A and detector 136B, using the combination of long pathway 142A, long pathway 142B, short pathway 140A, and short pathway 140B can be processed to generate a measure of regional oximetry (also called tissue oximetry). In one example, the calculation entails addition and subtraction of attenuations as detected by detector 136A and detector 136B. Detector 136A and detector 136B can include an optical transducer that provides an electrical signal corresponding to detected light.

The arrangement of optical elements (such as emitter 138A, emitter 138B, detector 136A, and detector 136B) and the number of optical elements (or transducers) can be configured for a particular purpose. In one example, contact surface 130A is arranged such that emitter 138A and emitter 138B are at opposing ends and detector 136A and detector 136B are located there between.

Figure 2:
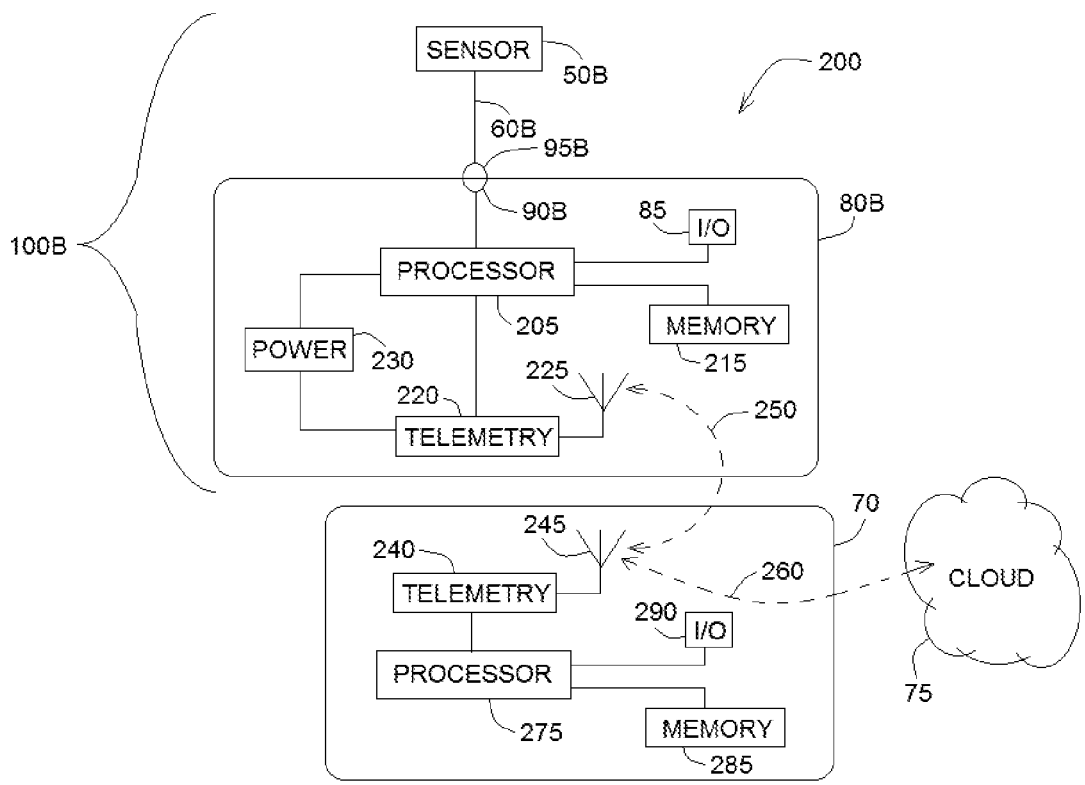
FIG. 2 illustrates a block diagram of a system, according to one example.

FIG. 2 illustrates a block diagram of system 200, according to one example. System 200 includes system 100B and remote device 70. In the example shown, system 100B includes sensor 50B and portable device 80B.

Sensor 50B is coupled by link 60B to connector 95B. Connector 95B is configured to mate with complementary connector 90B. Connector 90B is coupled to a housing of portable device 80B.

Portable device 80B includes processor 205. Processor 205 is configured to receive an electrical signal from sensor 50B and conducted by link 60B, connector 95B and connector 90B. Processor 205 can include a digital processor (such as a microprocessor) or an analog circuit. Processor 205 is coupled to memory 215. Memory 215 provides storage for data and instructions. Data stored in memory 215 can include measured (or calculated) data, calibration parameters or coefficients. Instructions stored in memory 215 can cause processor 205 to implement an algorithm. In one example, the algorithm includes selecting one of a plurality of calibration coefficients based on a particular identification signal corresponding to a particular sensor 50B coupled to connector 90B.

Processor 205 is coupled to I/O module 85. I/O module 85 can include user operable controls or switches and can include a visible display or indicator.

Processor 205 is coupled to telemeter module 220. Telemetry module 220, sometimes referred to as a communication module, enable wireless communication of data or instructions between portable device 80B and remote device 70. Telemetry module 220 is coupled to antenna 225 in the example shown. Telemetry module 220 can include a radio frequency (RF) transceiver, an infrared communication module, or an ultrasound (or audio) communication module.

Processor 205 and telemetry module 220 are coupled to power supply 230. Power supply 230 can include a rechargeable battery or a replaceable battery.

Portable device 80B can be configured as a hand-held device. In one example, portable device 80B is less than several inches in length and has a connector on a surface.

Remote device 70 can include a portable or mobile computing device (such as a cellular telephone, a laptop computer, a tablet computer) or can include a desktop computer, workstation, or a server.

Remote device 70 includes telemetry module 240 coupled to antenna 245. Telemetry module 240 (by way of antenna 245) is configured to communicate wirelessly with telemetry module 220 (by way of antenna 225).

Telemetry module 240 is coupled to processor 275. Processor 275, in one example, includes a digital processor. Processor 275 is coupled to I/O module 290 and coupled to memory 285. I/O module 290 can include a touch-sensitive display, a keyboard, a mouse, or other user operable interface. In addition, I/O module 290 can include a display, a network port, a printer, a speaker, or other output (or input/output) device.

In the example shown, antenna 245 and telemetry module 240 are coupled to a cloud or network 75 by link 260. Network 75 can include a wide area network or a local area network.

Figure 3:
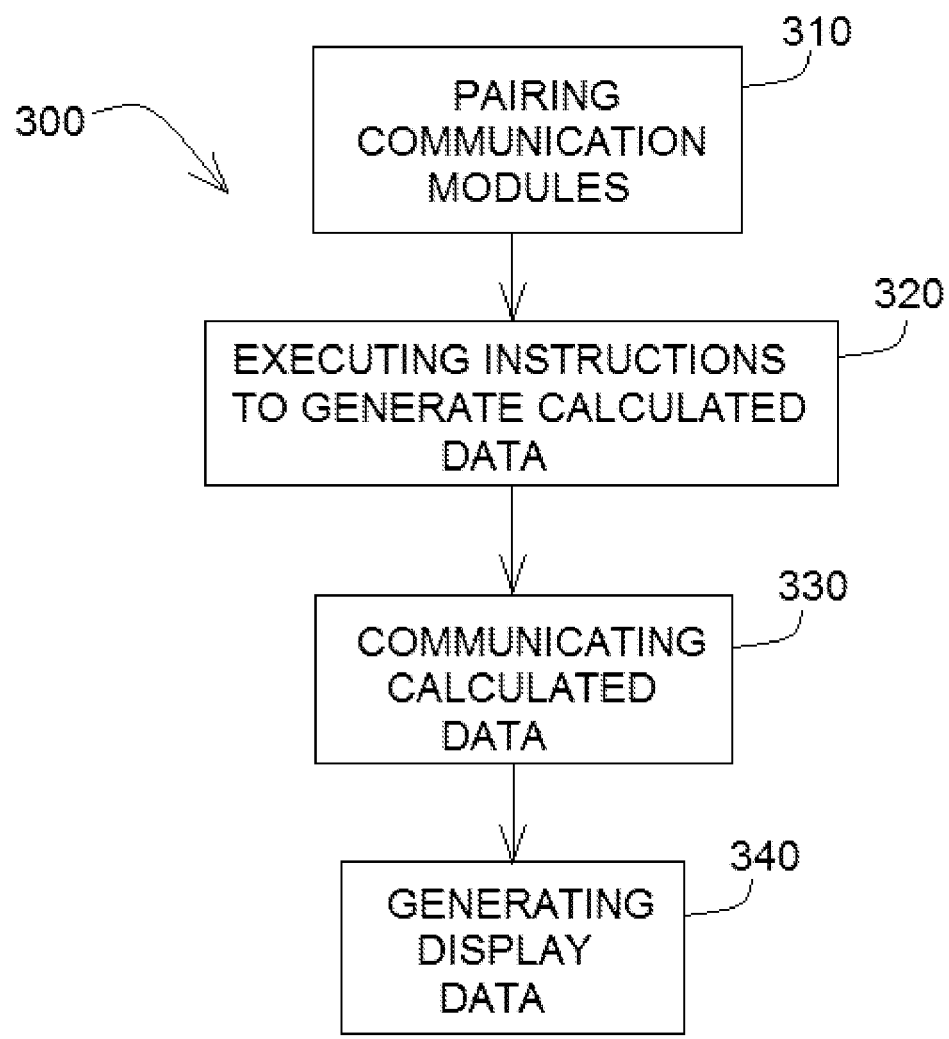
FIG. 3 illustrates a flow chart of a method executed by a system, according to one example.

FIG. 3 illustrates flow chart 300 implemented by a system, according to one example. Flow chart 300 includes, at 410, pairing communication modules. In one example, this entails establishing a wireless link between telemetry module 220 (and using antenna 225) and telemetry module 240 (and using antenna 245) in a process known as pairing. Pairing can include exchanging access credentials and coordinating handshaking protocols. Some communication protocols, such as Bluetooth, are paired by executing a predetermined algorithm.

At 320, method 300 includes executing instructions to generate calculated data based on a measured signal from sensor 50B. This can include executing instructions (stored in memory 215) using processor 205 to implement an algorithm. The algorithm can entail operating an emitter (such as emitter 138A or emitter 138B) according to a particular protocol and receiving an output signal from a detector (such as detector 136A or detector 136B). In one example, this can include receiving a temperature signal from a temperature transducer.

At 330, method 300 includes communicating the calculated data to remote device 70. Communicating can include sending and receiving a wireless signal (using wireless telemetry modules).

At 340, method 300 includes executing instructions using processor 275 to generate a visible display of data. The data can be displayed using I/O module 290. In one example, data is communicated to network 75 by telemetry module 240 and antenna 245 or communicated to network 75 by a network connection of I/O module 290.

Various Notes & Examples

Example 1 can include a system having a sensor, a second connector, a local processor, a first telemetry module, a second telemetry module, and a remote processor. The sensor is coupled to a cord. The cord has a first connector. The second connector is coupled to a housing. The second connector is configured to mate with the first connector. The local processor is coupled to the second connector and is disposed in the housing. The local processor is configured to execute instructions stored in a local memory. The local memory is disposed in the housing. The local processor is configured to generate calculated data based on a signal received at the second connector. The signal corresponds to a parameter measured by the sensor. The first telemetry module is coupled to the local processor and is configured to wirelessly communicate the calculated data. The second telemetry module is configured to communicate with the first telemetry module. The remote processor is coupled to the second telemetry module. The remote processor is configured to generate output data based on the calculated data.

Example 2 can include, or can optionally be combined with the subject matter of Example 1 to optionally include wherein the output data corresponds to regional oximetry.

Example 3 can include, or can optionally be combined with the subject matter of Example 1 to optionally include wherein the local processor is coupled to a user operable control.

Example 4 can include, or can optionally be combined with the subject matter of Example 1 to optionally include wherein the local processor is coupled to a visible display.

Example 5 can include, or can optionally be combined with the subject matter of Example 1 to optionally include wherein the local memory is configured to store the calculated data.

Example 6 can include, or can optionally be combined with the subject matter of Example 1 to optionally include wherein the first telemetry module includes a radio frequency transceiver.

Example 7 can include, or can optionally be combined with the subject matter of Example 1 to optionally include wherein the remote processor is configured to generate output data in near real-time relative to the signal.

Example 8 can include, or can optionally be combined with the subject matter of Example 1 to optionally include wherein the local memory is configured to store a plurality of calibration parameters and wherein the local processor is configured to select a particular calibration parameter from the plurality of calibration parameters, the particular calibration parameter corresponding to the sensor.

Example 9 can include, or can optionally be combined with the subject matter of Example 1 to optionally include wherein the sensor includes an optical element.

Example 10 can include, or can optionally be combined with the subject matter of Example 1 to optionally include wherein the local processor is coupled to a battery.

Example 11 can include, or can optionally be combined with the subject matter of Example 1 to optionally include wherein the housing is pocket-sized.

Example 12 can include, or can optionally be combined with the subject matter of Example 1 to optionally further include a cellular telephone and wherein at least one of the second telemetry module and the remote processor are included in the cellular telephone.

Example 13 can include a device having a first connector, a local processor, a local memory, and a local telemetry module. The first connector is coupled to a housing. The first connector is configured to mate with a sensor connector. The sensor connector is coupled to an optical sensor. The local processor is coupled to the housing. The local memory is coupled to the local processor. The local processor is configured to execute instructions stored in the local memory. The local processor is configured to generate calculated data based on a signal received at the first connector. The signal corresponds to a parameter measured by the optical sensor. The local telemetry module is coupled to the local processor and is configured to wirelessly communicate the calculated data.

Example 14 can include, or can optionally be combined with the subject matter of Example 13 to optionally include wherein the calculated data corresponds to regional oximetry.

Example 15 can include, or can optionally be combined with the subject matter of Example 13 to optionally include wherein the local processor is coupled to a user operable control.

Example 16 can include, or can optionally be combined with the subject matter of Example 13 to optionally include wherein the local processor is coupled to a visible display.

Example 17 can include, or can optionally be combined with the subject matter of Example 13 to optionally include wherein the local memory is configured to store the calculated data.

Example 18 can include, or can optionally be combined with the subject matter of Example 13 to optionally include wherein the local telemetry module includes a radio frequency transceiver.

Example 19 can include, or can optionally be combined with the subject matter of Example 13 to optionally include wherein the local telemetry module is configured to wirelessly communicate the calculated data in near real-time relative to the signal.

Example 20 can include, or can optionally be combined with the subject matter of Example 13 to optionally include wherein the local memory is configured to store a plurality of calibration parameters and wherein the local processor is configured to select a particular calibration parameter from the plurality of calibration parameters, the particular calibration parameter corresponding to the optical sensor.

Example 21 can include, or can optionally be combined with the subject matter of Example 13 to optionally include wherein the local processor is coupled to a battery.

Example 22 can include, or can optionally be combined with the subject matter of Example 13 to optionally include wherein the housing is pocket-sized.

Example 23 can include a method including pairing communication modules, executing instructions to generate calculated data, communicating the calculated data, and generating display data. The method includes pairing a first communication module of a remote computing device with a second communication module of a portable device. The portable device has a local connector configured to mate with a sensor connector. The sensor connector is configured to provide a measured signal from an optical sensor. The local connector is coupled to a local processor. The method includes executing instructions using the local processor. The instructions are stored in a local memory. The instructions are configured to generate calculated data based on the measured signal. The measured signal corresponds to tissue at a contact surface of the optical sensor. The method includes communicating the calculated data to the remote computing device using the first communication module and using the second communication module. The method includes generating display data for a display of the remote computing device based on the calculated data.

Example 24 can include, or can optionally be combined with the subject matter of Example 23 to optionally include wherein executing the instructions using the local processor includes calculating a temperature using a temperature transducer.

Example 25 can include, or can optionally be combined with the subject matter of Example 23 to optionally include wherein executing the instructions using the local processor includes emitting light from the optical sensor.

Example 26 can include, or can optionally be combined with the subject matter of Example 23 to optionally include wherein executing instructions using the local processor includes calculating regional oximetry.

Example 27 can include, or can optionally be combined with the subject matter of Example 23 to optionally include displaying regional oximetry data based on the display data using the display.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system comprising:
   a sensor coupled to a cord, the cord having a first connector;
   a second connector coupled to a housing, the second connector configured to mate with the first connector;
   a local processor coupled to the second connector and disposed in the housing, the local processor configured to execute instructions stored in a local memory, the local memory disposed in the housing and the local processor configured to generate calculated data based on a signal received at the second connector, the signal corresponding to a parameter measured by the sensor, wherein the local processor includes an analog processor or a digital processor;
   a first telemetry module coupled to the local processor and disposed in the housing, the first telemetry module configured to wirelessly communicate the calculated data;
   a second telemetry module configured to communicate with the first telemetry module;
   a remote processor coupled to the second telemetry module, the remote processor configured to generate output data based on the calculated data; and
   wherein the local memory is configured to store a plurality of calibration parameters and wherein the local processor is configured to select a particular calibration parameter from the plurality of calibration parameters, the particular calibration parameter corresponding to the sensor, and wherein the calculated data communicated by the first telemetry module is based on an identification signal corresponding to the sensor and wherein the calculated data is based on the selected calibration parameter, and wherein the first telemetry module includes a radio frequency transceiver.

2. The system of claim 1 wherein the output data corresponds to regional oximetry.

3. The system of claim 1 wherein the local processor is coupled to a user operable control.

4. The system of claim 1 wherein the local processor is coupled to a visible display.

5. The system of claim 1 wherein the local memory is configured to store the calculated data.

6. The system of claim 1 wherein the remote processor is configured to generate output data in near real-time relative to the signal.

7. The system of claim 1 wherein the sensor includes an optical element.

8. The system of claim 1 wherein the local processor is coupled to a battery.

9. The system of claim 1 wherein the housing is pocket-sized.

10. The system of claim 1 further including a cellular telephone and wherein at least one of the second telemetry module and the remote processor are included in the cellular telephone.

11. A device comprising:
    a first connector coupled to a housing, the first connector configured to mate with a sensor connector, the sensor connector coupled to an optical sensor;
    a local processor disposed in the housing, wherein the local processor includes an analog processor or a digital processor;
    a local memory coupled to the local processor and disposed in the housing, the local processor configured to execute instructions stored in the local memory, the local processor configured to generate calculated data based on a signal received at the first connector, the signal corresponding to a parameter measured by the optical sensor;
    a local telemetry module disposed in the housing and coupled to the local processor and configured to wirelessly communicate the calculated data; and
    wherein the local memory is configured to store a plurality of calibration parameters and wherein the local processor is configured to select a particular calibration parameter from the plurality of calibration parameters, the particular calibration parameter corresponding to the optical sensor, and wherein the calculated data communicated by the local telemetry module is based on an identification signal corresponding to the sensor and wherein the calculated data is based on the selected calibration parameter, and wherein the local telemetry module includes a radio frequency transceiver.

12. The device of claim 11 wherein the calculated data corresponds to regional oximetry.

13. The device of claim 11 wherein the local processor is coupled to a user operable control.

14. The device of claim 11 wherein the local processor is coupled to a visible display.

15. The device of claim 11 wherein the local memory is configured to store the calculated data.

16. The device of claim 11 wherein the local telemetry module is configured to wirelessly communicate the calculated data in near real-time relative to the signal.

17. The device of claim 11 wherein the local processor is coupled to a battery.

18. The device of claim 11 wherein the housing is pocket-sized.

* * * * *